United States Patent
Zhang et al.

(10) Patent No.: US 12,163,941 B2
(45) Date of Patent: Dec. 10, 2024

(54) METHOD AND DEVICE FOR MONITORING COMPREHENSIVE GROWTH OF POTTED LETTUCE

(71) Applicant: JIANGSU UNIVERSITY, Zhenjiang (CN)

(72) Inventors: Xiaodong Zhang, Zhenjiang (CN); Xuewei Zhang, Zhenjiang (CN); Hanping Mao, Zhenjiang (CN); Baijing Qiu, Zhenjiang (CN); Hongtao Zhang, Zhengzhou (CN); Zhiyu Zuo, Zhenjiang (CN); Hongyan Gao, Zhenjiang (CN); Jiheng Ni, Zhenjiang (CN); Yixue Zhang, Zhenjiang (CN); Fang Zhang, Zhenjiang (CN)

(73) Assignee: JIANGSU UNIVERSITY, Zhenjiang (CN)

( * ) Notice: Subject to any disclaimer, the term of this patent is extended or adjusted under 35 U.S.C. 154(b) by 1172 days.

(21) Appl. No.: 16/771,708

(22) PCT Filed: Dec. 19, 2017

(86) PCT No.: PCT/CN2017/117191
§ 371 (c)(1),
(2) Date: Nov. 10, 2020

(87) PCT Pub. No.: WO2019/113998
PCT Pub. Date: Jun. 20, 2019

(65) Prior Publication Data
US 2021/0056685 A1  Feb. 25, 2021

(30) Foreign Application Priority Data
Dec. 11, 2017 (CN) .......................... 201711309708.5

(51) Int. Cl.
*G01N 33/48* (2006.01)
*G01N 21/3563* (2014.01)
(Continued)

(52) U.S. Cl.
CPC ..... *G01N 33/0098* (2013.01); *G01N 21/3563* (2013.01); *G06F 17/11* (2013.01);
(Continued)

(58) Field of Classification Search
CPC ............ G01N 33/0098; G01N 21/3563; G06F 17/11; G06T 7/0012; G06T 7/194; G06T 2207/10048; G06T 2207/30188
See application file for complete search history.

(56) References Cited

FOREIGN PATENT DOCUMENTS

| CN | 103293111 A | 9/2013 |
|---|---|---|
| CN | 103439265 A | 12/2013 |

(Continued)

OTHER PUBLICATIONS

Zhou et al. Visualization research of moisture content in leaf lettuce leaves based on WT-PLSR and hyperspectral imaging technology. Journal of Food Process Engineering, vol. 41, Nov. 2017, article e12647, 7 pages.*

*Primary Examiner* — Russell S Negin
(74) *Attorney, Agent, or Firm* — Bayramoglu Law Offices LLC

(57) ABSTRACT

An apparatus for monitoring comprehensive growth condition of potted lettuce consists of a polarized hyperspectral imaging system and a 3D laser scanning system. The polarized hyperspectral imaging system includes a control system, a dual-coordinate sample holder, an image acquisition system, and a light source system, and the polarized hyperspectral imaging system detects water and fertilizer stress in lettuce by polarized hyperspectral multi-dimensional reflection imaging of characteristics on a canopy/leaf scale. The (Continued)

3D laser scanning system detects morphological characteristics such as the biomass, stem diameter, plant height, and leaf area of lettuce. The method includes: step 1: culturing samples: cultivating the potted lettuce under a water stress, and under a nitrogen stress and water stress; step 2: acquiring morphological data of an entire lettuce plant; step 3: processing and analyzing data; step 4: correcting a model by using a water compensation factor; step 5: establishing a multi-characteristic integration model.

6 Claims, 6 Drawing Sheets

(51) Int. Cl.
    *G01N 33/00*     (2006.01)
    *G01N 33/50*     (2006.01)
    *G06F 17/11*     (2006.01)
    *G06T 7/00*     (2017.01)
    *G06T 7/194*     (2017.01)
    *G06V 10/40*     (2022.01)
    *G06V 10/56*     (2022.01)

(52) U.S. Cl.
    CPC ............ *G06T 7/0012* (2013.01); *G06T 7/194* (2017.01); *G06V 10/40* (2022.01); *G06V 10/56* (2022.01); *G06T 2207/10048* (2013.01); *G06T 2207/30188* (2013.01)

(56) References Cited

FOREIGN PATENT DOCUMENTS

| | | |
|---|---|---|
| CN | 104614321 A | 5/2015 |
| CN | 106197317 A | 12/2016 |
| CN | 106406403 A | 2/2017 |
| JP | 3885046 B2 | 2/2007 |

* cited by examiner (a) (b)

(c) (d)

METHOD AND DEVICE FOR MONITORING COMPREHENSIVE GROWTH OF POTTED LETTUCE

CROSS REFERENCE TO THE RELATED APPLICATIONS

This application is the national stage entry of International Application No. PCT/CN2017/117191, filed on Dec. 19, 2017, which is based upon and claims priority to Chinese Patent Application No. 201711309708.5, filed on Dec. 11, 2017, the entire contents of which are incorporated herein by reference.

TECHNICAL FIELD

The present invention relates to the technical field of bioinformatic detection in facility agriculture, and in particular, to a method and an apparatus for monitoring comprehensive growth condition of potted lettuce.

BACKGROUND

At present, relatively underdeveloped environmental control equipment is used in greenhouses, especially, sunlight greenhouses and steel-frame greenhouses used by middle- and small-scale farmers in China. Water supply, fertilizer use, and environmental regulation mainly depend on conventional experience, or regulation is performed according to set values. The growth information of crop and a dynamic change process of the growth information are not considered. Dynamic regulation cannot be performed according to actual requirements of crop. Therefore, there is an urgent need to accurately monitor the growth condition, nutrient information, and growth process of crop and determine the growth status of the crop, to implement accurate regulation based on the growth requirement of the crop.

Currently, lossless monitoring methods such as hyperspectral remote sensing, visual image detection, and 3D scanning detection technologies are mainly used to implement the lossless monitoring of crop information. The lossless monitoring methods are fast and efficient and cause no harm to crop, and therefore gradually become the focus of the lossless monitoring of nutrients. In a lossless diagnosis method based on a reflective spectrum technology, a point source sampling manner is usually used to reflect comprehensive reflection characteristics in a sampling area. Although multi-band combined characteristics can be used to implement the inversion of nutrient information of crop, differences in light reflection characteristics in an entire leaf area and slight differences in color texture, the distribution of the color texture, and the like on the leaf surface cannot be reflected. A visual sensor has relatively high resolution and a relatively large field of view range. The impact of factors such as the background can be eliminated by using an image segmentation technology, to overcome the disadvantages that a spectral method has a relatively small test range and there is a relatively strict requirement for a test position. Therefore, more crop information can be obtained. However, a conventional visual sensor usually has the problem of relatively low optical spectrum resolution, and usually obtains a single color image in a visible light range (400 nm to 700 nm). Image characteristics in different bands cannot be extracted and analyzed. In a hyperspectral image technology, cube data, formed by hundreds of hyperspectral images at different wavelengths, of a monitoring object within visible light and near infrared ranges from 400 nm to 1700 nm can be obtained at relatively high spectral resolution of 3 nm to 10 nm, to synchronously acquire and analyze the reflection spectrum of crop leaf and reflection strength distribution image information of leaf in different spectral bands, thereby achieving advantages that conventional optical spectrum and image technology does not have. The abundance or scarcity of nutrients and water for crop directly determines differences in the biomass, leaf area, stem diameter, plant height, leaf angle, and the like of the crop, and therefore may also be used as valid characteristics to implement the inversion of nutrients and water. Overall morphological characteristics of a plant can be obtained from a conventional visual image. However, the measurement precision is not high.

SUMMARY

For the deficiencies in the prior art, an object of the present invention is to provide a method and an apparatus for monitoring comprehensive growth condition of potted lettuce, to implement fast, lossless, accurate detection of lettuce under water and fertilizer stress, to provide reference for the scientific management of a greenhouse environment as well as water supply and fertilizer use.

The present invention achieves the foregoing technical object by using the following technical measure.

A method for monitoring comprehensive growth condition of potted lettuce is characterized by mainly including the following steps:

Step 1: culturing samples first: cultivating lettuce under water stress, and cultivating lettuce under nitrogen and water stress;

Step 2: acquiring morphological data of an entire lettuce plant:

2.1 acquiring 3D laser scanning imaging data by using a handheld, self-positioning, 3D laser scanner:

1) before scanning is performed, first bonding black-contour high-reflectivity target dots with a diameter of 6 mm on a leaf and a pot of a crop to be scanned, the shortest distance between two target dots being controlled to be 15 mm; and 2) operating the scanner, measuring a calibration board by using the 3D laser scanner to correct parameters of a sensor, and sequentially obtaining 3D data of all crop samples in a handheld scanning mode; and 2.2 acquiring polarized hyperspectral imaging data by using a polarized hyperspectral imaging system:

1) placing a sample 1 on a displacement stage 2 of the polarized hyperspectral imaging system, setting a wavelength range of a uniform light source system 7 to 300 nm to 2200 nm, setting a light intensity range to 6500 lux, and adjusting the geometric center of the imaging system to be consistent with the geometric center of the horizontal axis X and the vertical axis Z of the displacement stage;

2) using the two hyperspectral imaging systems 5-1 and 5-2 each having a front polarizing filter set, sampling polarization angles of polarizers being 0°, 45°, 90°, 135°, and 180°, transmission wavelengths of hyperspectral front filters being 402 nm, 446 nm, 556 nm, 636 nm, 699 nm, 706 nm, 775 nm, 960 nm, and 1420 nm, and separately performing push-broom, polarized hyperspectral scanning imaging in the horizontal direction and the vertical direction, to obtain polarized hyperspectral feature images in the front-view direction and the top-view direction;

3) extracting hyperspectral feature images of a sample under nutrient and water stress in the front-view and top-view fields of view by performing coordinate matching and integration of front-view/top-view feature images, and extracting images of the crown spread, plant height, and leaf angle of the plant;

4) extracting hyperspectral feature images of the canopy at characteristic wavelengths based on 402-nm, 446-nm, 556-nm, 636-nm, 699-nm, 706-nm, 775-nm, 960-nm, and 1420-nm front filters, and extracting feature parameters such as the venation distribution, average grayscale, and leaf margin shaded area of the leaf surface at hyperspectral nutrient- and water-sensitive wavelengths of 402 nm, 446 nm, 556 nm, 636 nm, 699 nm, 706 nm, 775 nm, 960 nm, and 1420 nm; and 5) extracting polarization state, Stokes vector, Mueller matrix variables of the plant sample under nitrogen and water stress based on obtained polarized hyperspectral images of 402 nm, 446 nm, 556 nm, 636 nm, 699 nm, 706 nm, 775 nm, 960 nm, and 1420 nm at characteristic polarization angles of 0°, 45°, 90°, 135°, and 180°;

Step 3: processing and analyzing data:

3.1 modeling the 3D laser scanning imaging data:

(1) repairing a model by using the reverse engineering software Geomagic Qualify, to overcome scanning defects to obtain an optimal lettuce model;

1) importing the obtained 3D data of lettuce into the software Geomagic Qualify, converting the lettuce model formed by triangles into a point cloud, and eliminating excessive noise by using the software;

2) converting the 3D point cloud by encapsulation into a curved surface model formed by triangles, and filling hole parts in the surface of lettuce; and 3) finally performing smoothing on the lettuce model; and (2) modeling the biomass, leaf area, plant height, and stem diameter of lettuce: volume calculation:

1) segmenting lettuce data at equal intervals with a step length of a in the plant height direction, that is, the Z axis direction, to obtain n layers of lettuce segments, wherein the step length a is far less than the thickness of a lettuce leaf, when a tends toward the infinitesimal, n tends toward infinity, and it may be considered that the volume of lettuce is formed by n layers of irregular graphs with the bottom area of $S_k$ and the height of a; and 2) calculating the cross-sectional area $S_k$ of each layer of segmented lettuce: projecting point cloud data of each layer of lettuce onto an X-Y plane perpendicular to the plant height direction, and segmenting the data at equal intervals with a step length of a at the same time respectively in the X axis direction and the Y axis direction, to generate i×j pixel cells; determining each pixel cell according to point cloud data projected into the pixel cell of each layer of segmented lettuce, wherein when the pixel cell includes the projected point cloud data of the lettuce, the pixel cell is a valid pixel cell and is labeled as 1, or otherwise, when the pixel cell does not include the point cloud data, the pixel cell is labeled as 0; and counting a quantity M of valid pixel cells, and calculating a product of multiplying the quantity of valid pixel cells by the area of a unit pixel cell as the cross-sectional area of the layer of lettuce, formulas for calculating the volume of lettuce being:

$$S_k = aaM \quad (1),$$

and $$V = \Sigma_{i=1}^{n} S_k = \Sigma_{i=1}^{n} aaM \quad (2),$$

wherein in the formulas, V is the volume of lettuce, $S_k$ is the cross-sectional area of lettuce, a is the step length, and M is the quantity of valid pixel cells; and establishing, based on measured values of the obtained volume of the lettuce and the obtained fresh weight of the lettuce, a biomass monitoring model that is based on 3D scan data:

$$B_m = 0.13 + 0.91V \quad (3),$$

wherein in the formula, $B_m$ is the biomass of the lettuce;

leaf area calculation:

interpolating the point cloud data to form an irregular triangle mesh, calculating the area $S_i$ of each triangle, and performing addition on the areas to calculate the leaf area $S_c$, a formula for calculating the leaf area of lettuce being:

$$S_c = \Sigma_{i=1}^{n} S_i \quad (4);$$

plant height calculation:

assuming that the coordinates of any point in the point cloud data are f(x, y, z), wherein it is only necessary to calculate the maximum value $z_{max}$ and the minimum value $z_{min}$ of the lettuce model in the Z axis direction, labeling that the coordinate point of the maximum value $z_{max}$ is $f(x_1, y_1, z_1)$ and the coordinate point of the minimum value $z_{min}$ is $f(x_2, y_2, z_2)$, and calculating the distance between the two coordinate points by using the following formula to obtain the plant height $P_h$:

$$P_h = z_{max} - z_{min} = z_1 - z_2 \quad (5);$$

stem diameter calculation:

capturing lettuce stem cross sections at intervals of 3.3 mm from the bottom of a permanent plant pot in the plant height direction, capturing three cross sections, calculating the diameter of each cross section, and calculating an average value of the cross sections to calculate the stem diameter of the lettuce, wherein the image of the lettuce stem cross section is formed by a layer of point cloud approximate to a circle, and the maximum value $x_{max}$ and the minimum value $x_{min}$ in the X axis direction and the maximum value $y_{max}$ and the minimum value $y_{min}$ in the Y axis direction are calculated in the X-Y plane to calculate the diameter of the cross section, as shown in FIG. 5, a formula for calculating the stem diameter of the lettuce being:

$$L_a = \Sigma_{i=1}^{3} [(x_{i\,max} - x_{i\,min}) + (y_{i\,max} - y_{i\,min})]/6 \quad (6),$$

wherein in the formula, $L_a$ is the stem diameter of the lettuce, $z_{imax}$ and $x_{imin}$ are respectively the maximum value and the minimum value of an $i^{th}$ layer (i=1, 2 or 3) of cross-sectional image in the X axis direction, and $y_{imax}$ and $y_{imin}$ are respectively the maximum value and the minimum value of the $i^{th}$ layer of cross-sectional image in the Y axis direction; and establishing a lettuce nitrogen monitoring model by using a lettuce sample:

$$N=13.26-0.24L_a+0.15P_h+7.1\times10^{-6}S_c+0.03B_m \quad (7),$$

wherein a correlation coefficient of the model is 0.90, and a root-mean-square deviation is 0.87; and 3.2 modeling polarized hyperspectral image data:

(1) performing background segmentation on a polarized hyperspectral image; and
1) first using a characteristic that there is a largest grayscale difference between a target image at 476 nm and the background, to segment a target image of lettuce by using a bimodal method;
2) performing grayscale inversion on a binarized target image, filling residues, and eliminating solitary noise; and
3) performing a pixel multiplication operation on the original hyperspectral image and the processed binarized target image, to eventually obtain a hyperspectral sequence target image of lettuce leaf; and (2) extracting a polarized hyperspectral feature wavelength;
1) screening nitrogen features by using a sensitive range stagewise and stepwise regression method, and obtaining, by using an adaptive band selection (ABS) method, indices from an image with variables of stepwise regression selection;
2) obtaining an index list according to the ABS method, performing sorting according to the values of the indices, and eventually selecting wavelengths with large image indices as nitrogen feature wavelengths, the wavelengths being 402 nm, 446 nm, 556 nm, 636 nm, 699 nm, and 706 nm;
3) extracting, by using the ABS method, feature wavelengths that can best represent water, and using grayscale average values at the feature wavelengths of 775 nm, 960 nm, and 1420 nm for water features of the lettuce; and
4) obtaining the venation distribution, average grayscale, and leaf margin shaded area at nutrient- and water-sensitive wavelengths and the polarization state, Stokes vector, Mueller matrix variables of feature images of 402 nm, 446 nm, 556 nm, 636 nm, 699 nm, 706 nm, 775 nm, 960 nm, and 1420 nm at characteristic polarization angles of 0°, 45°, 90°, 135°, and 180°;

Step 4: Correcting a Model by Using a Water Compensation Factor:

using the grayscale average values at the feature wavelengths of 775 nm, 960 nm, and 1420 nm to represent a water feature of lettuce, analyzing water content features of crop nitrogen images in different characteristic spectral bands, establishing water content response models of lettuce leaf in different characteristic spectral bands, and compensating for a nitrogen feature of lettuce, a specific process thereof being:
1) performing partial least squares regression (PLSR) on a grayscale variable of a water content feature image of a sample and a measured value of water content to establish a lettuce water content prediction model:

$$W=65.09+43.82AG_{775}+12.65AG_{960}-117.72AG_{1420} \quad (8),$$

wherein in the formula, $AG_{775}$, $AG_{960}$, and $AG_{1420}$ represent grayscale average values of a lettuce leaf image at sensitive wavelengths of 775 nm, 960 nm, and 1420 nm, and W is a measured value of water content of leaf;

2) performing hierarchical compensation of nitrogen features according to a water content level of a prediction sample of the monitoring model and based on differences in reflection responses at different water content levels, wherein in the case of an estimated water content level, a change rate $\Delta W_i$ of a nitrogen hyperspectral image eigenvariable $AG_i$ (i=1, 2, . . . , and 6) in the sample along with a water content level at the same nitrogen content level may be calculated by combining total nitrogen content in a sample obtained through AA3 chemical testing and a reflectivity value at a nitrogen optical spectrum feature wavelength, correction coefficients $\Delta AG_i$ for the eigenvariable $AG_i$ at different water content levels may be calculated accordingly, as shown in Table 6, and the nitrogen hyperspectral image eigenvariable $AG_i$ is corrected according to Formula (9):

$$AG_i'=AG_i*(1+\Delta AG_i), (i=1,2,\ldots,\text{and }6) \quad (9);$$

and 3) establishing the nitrogen monitoring model based on obtained hyperspectral image characteristics of lettuce nitrogen in different spectral bands, by using characteristic compensation, and by using a partial least squares (PLS) method:

$$N=23.39+6.14AG_{402}+25.66AG_{446}-31.52AG_{556}+66.85AG_{636}+45.65AG_{699}-56.76AG_{706} \quad (10);$$

Step 5: Establishing a Multi-Characteristic Integration Model:

performing information integration based on the obtained polarized hyperspectral image characteristics and growth condition characteristics such as the stem diameter, plant height, leaf area, and biomass and by using PLSR, and establishing a lettuce nitrogen multi-characteristic monitoring model;
1) first respectively performing normalization on two different types of eigenvariables by using Formula (11):

$$x_i'=(x_i-x_{min}(x_{max}-x_{min}) \quad (11),$$

wherein in the formula, x is an eigenvalue of an eigenvector, i is an eigen number (i=1, 2, 3, . . . ), and $x_{min}$ and $x_{max}$ are respectively the minimum value and the maximum value of a sample eigenvalue in the eigenvector; and
2) performing PLS correlation analysis on normalized six image characteristics and four growth condition characteristics, and establishing a PLS nitrogen regression model that is based on original variables:

$$N=-4.72+12.34AG_{402}-8.52AG_{446}+34.71AG_{556}-26.73AG_{636}+10.94AG_{699}-15.62AG_{706}+7.53L_a-11.42P_h-15.91S_c+18.95B_m \quad (12);$$

Step 6: performing random sampling to acquire information under water and fertilizer stress in actual greenhouse production work, repeating Step 2 and Step 3, obtaining data of crop under water and fertilizer stress, and importing the data into the system for analysis and calculation, to obtain quantified results under nitrogen and water stress; and Step 7: obtaining comprehensive growth condition information of potted lettuce by using quantified results under water and fertilizer stress and according to the PLS nitrogen regression model that is based on the original variables.

Further, lettuce is cultivated under water stress at four levels in Step 1, concentrates with 25%, 50%, 75%, and 100% of the standard water content are respectively used for four water level irrigation amounts, water-stressed samples are individually processed in the following manner: in a first group (W1), a nutrient solution and water are supplied to crop by using a standard formula and a normal irrigation amount throughout the entire experiment; in a second group (W2), standard irrigation is performed twice during the experiment, the concentrate is only irrigated for one minute at 8 o'clock every day during the remaining time, and the concentrate is a nutrient solution that is obtained through proportional concentration according to a nutrient solution irrigation amount required for one day in a corresponding growth stage by using a standard nutrient solution formula and according to irrigation for one minute, to guarantee various nutrients required for the growth of the plant; in a third group (W3), standard irrigation is performed once in the middle stage of the experiment, and the concentrate is also only irrigated for one minute at 8 o'clock every day during the experiment; and in a fourth group (W4), irrigation is not performed throughout the entire experiment, the concentrate is only applied for one minute every day.

Further, lettuce is cultivated under nitrogen stress at four levels in Step 1, the nitrogen content at the four levels is respectively 25%, 50%, 100%, and 200% of that in the standard formula, and nutrients and water are supplied to samples by using a timed drip irrigation apparatus; during the seeding stage of crop, a nutrient solution is irrigated once in the morning every day; in the middle and later stages of the growth of crop, the nutrient solution is irrigated once in the morning and once in the afternoon every day, and irrigation lasts five minutes each time; the timed on or off of a timer is controlled to control the supply of the nutrient solution; and the four nitrogen levels are specifically: in a first group (A), based on the standard formula, without changing other nutrient elements, the amount of nitrogen element is reduced to 25% of that in the standard formula, and $Ca^{2+}$, $K^+$, and $PO_4^{-3}$ that are reduced along with the nitrogen element are supplemented by using $CaCl_2$, KCl, and $KH_2PO_4$; in a second group (B), based on the standard formula, the nitrogen element is reduced to 50% of that in the standard formula, and $Ca^{2+}$, $K^+$, and $PO_4^{-3}$ that are reduced along with the nitrogen element are supplemented by using $CaCl_2$, KCl, and $KH_2PO_4$; in a third group (C), a normal nutrient solution is configured according to the standard formula; and in a fourth group (D), based on the standard formula, the nitrogen element is doubled, and the nitrogen element is supplemented by using $NaNO_3$ and $CO(NH_2)_2$.

Further, during the acquisition of the 3D laser scanning imaging data in step 2, the target dots are bonded to two semicircular pieces of white paper, the distance between the target dots is controlled to be 100 mm, and the two semicircular pieces of white paper are spliced into one circular piece and placed on the plane of the upper edge of a pot.

Further, during the acquisition of 3D laser scanning imaging data, the laser power of the 3D laser scanner is 65%, the shutter time is 7.2 ms, and the resolution is 0.50 mm.

An apparatus for monitoring comprehensive growth condition of potted lettuce is characterized by including a polarized hyperspectral image monitoring system, a 3D laser scanning system, a data processing module, and a monitoring module, wherein the polarized hyperspectral image monitoring system includes a control system, a dual-coordinate sample holder 2, an image acquisition system, and a light source system;

the image acquisition system includes two polarized hyperspectral imaging systems 5, an image acquisition device 9, a vertical boom 3, and a cantilever 4; the vertical boom 3 consists of a base 3-1, a vertical rod 3-2 with a lead screw, and a first slide 3-3, the base 3-1 is fixed on the left side of the bottom of a light box 12 by a screw, the upper portion of the base 3-1 is connected to the vertical rod 3-2 by a hinge, and the vertical rod 3-2 is swingable transversely with the hinge as the center, to complete the adjustment of the spatial pose of an imaging device; the first slide 3-3 is mounted on the vertical rod 3-2; and a first polarized hyperspectral imaging system 5-1 is mounted on the first slide 3-3, and the first slide 3-3 is movable vertically along the vertical rod 3-2 under the drive of the lead screw, to drive the first polarized hyperspectral imaging system 5-1 to search for an optimal monitoring position, to acquire polarized hyperspectral image information in the front-view direction;

the cantilever 4 consists of a base 4-1, a cross rod 4-2 with a lead screw, and a second slide 4-3, the base 4-1 is fixed at the upper portion of the right side plate of the light box 12 by a screw, the base 4-1 is connected to the cross rod 4-2 by a hinge, and the cross rod 4-2 is swingable vertically with the hinge as the center, to complete the adjustment of the spatial pose of the imaging device; and the second slide 4-3 is mounted on the cross rod 4-2, a second polarized hyperspectral imaging system 5-2 is mounted on the second slide 4-3, and the second slide 4-3 is movable transversely in the horizontal direction along the cross rod 4-2 under the drive of the lead screw, to drive the second polarized hyperspectral imaging system 5-2 to search for an optimal monitoring position, to acquire the polarized hyperspectral image information in the top-view direction;

the light source system consists of a visible light-near infrared light source 7 and a tripod head 6, one tripod head 6 is respectively mounted at the bottom end and the top end of the vertical rod 3-2 and the right end and the left end of a vertical rod 4-2, the visible light-near infrared light source 7 is respectively mounted on each tripod head, and the tilt of the visible light-near infrared light source 7 is capable of being set by using the tripod head 6, to implement clear and uniform imaging of the plant;

the dual-coordinate sample holder 2 is fixed at the geometric center position of the bottom plane of the light box 12, 2-1 is a horizontal lead screw, 2-2 is a vertical lead screw, a sample carrier is mounted at the top end of the vertical lead screw 2-2 and is used for placing a to-be-tested sample 1, and the horizontal lead screw 2-1 and the vertical lead screw 2-2 move to drive the sample carrier to displace uniformly in the horizontal direction and the vertical direction, to cooperate with the image acquisition system to implement the scanning and imaging of the push broom polarized hyperspectral imaging system 5-1 and polarized hyperspectral imaging system 5-2;

the polarized hyperspectral imaging system 5 consists of a front polarizer, a polarizer driving apparatus, a front filter, a filter switching apparatus, a spectrograph, and an imaging system from front to rear, the polarizer is located at the foremost end of the entire system and is rotatable by 360° under the drive of the polarizer driving apparatus, to set any polarization angle, and the spectrograph and the imaging system set the polarization angle and acquire polarization information; and narrowband filters of 402 nm, 446 nm, 556 nm, 636 nm, 699 nm, 706 nm, 775 nm, 960 nm, and 1420 nm are located behind the polarizer, and a wheel switching manner is used for the filter, to cooperate with the spectrograph and the imaging system to acquire front-view and top-view hyperspectral feature images of a crop sample under nutrient and water stress;

the control system includes a control computer 11, a light source controller 10, the image acquisition device 9, and a movement controller 8;

the light source controller 10 is connected to the visible light-near infrared light source 7, to implement light source control with different light intensity and light quality;

the image acquisition device 9 is connected to the two polarized hyperspectral imaging systems 5 and the control computer 11, and the control computer 11 sends an instruction to acquire front-view and top-view imaging information of the polarized hyperspectral imaging system 5;

the 3D laser scanning system is also connected to the control computer 11 and is used for acquiring 3D laser scanning and imaging data; and the data processing module and the monitoring module are built in the control computer 11, the data processing module is configured to: repair a lettuce model according to the 3D laser scanning and imaging data, establish a biomass model, a leaf area model, a plant height model, and a stem diameter model of lettuce, and calculate the volume, leaf area, plant height, and stem diameter; and perform background segmentation on a polarized hyperspectral image and extract a feature wavelength according to polarized hyperspectral image data, to obtain the venation distribution, average grayscale, and leaf margin shaded area at nutrient- and water-sensitive wavelengths and polarization state, Stokes vector, Mueller matrix variables of feature images of 402 nm, 446 nm, 556 nm, 636 nm, 699 nm, 706 nm, 775 nm, 960 nm, and 1420 nm at characteristic polarization angles of 0°, 45°, 90°, 135°, and 180°; and the monitoring module obtains comprehensive growth condition information of potted lettuce according to the data obtained by the data processing module, based on a lettuce water content prediction model and a nitrogen monitoring model, and according to a PLS nitrogen regression model that is based on original variables, wherein the lettuce water content prediction model is:

$$W=65.09+43.82AG_{775}+12.65AG_{960}-117.72AG_{1420},$$

the nitrogen monitoring model is:

$$N=23.39+6.14AG_{402}+25.66AG_{446}-31.52AG_{556}+66.85AG_{636}+45.65AG_{699}-56.76AG_{706}, \text{ and}$$

the PLS nitrogen regression model that is based on the original variables is:

$$N=-4.72+12.34AG_{402}-8.52AG_{446}+34.71AG_{556}-26.73AG_{636}+10.94AG_{699}-15.62AG_{706}+7.53L_a-11.42P_h-15.91S_c+18.95B_m.$$

The movement controller 8 is connected to the dual-coordinate sample holder 2, the vertical boom 3, the cantilever 4, and the tripod head 6; and at the same time, the movement controller 8 is connected to the control computer 11, and the control computer 11 sends instructions to control the vertical displacement and the horizontal displacement of the dual-coordinate sample holder 2, control the slide drive of the vertical boom 3 and the cantilever 4, and control the tilt of the tripod head 6.

The polarization characteristic may accurately represent the leaf surface quality and microstructural characteristics of leaf under water and fertilizer stress. In the present invention, the polarized hyperspectral image technology can be constructed to analyze the characteristics such as the reflection strength, color, texture, and surface quality on the crop/canopy leaf scale. However, for differences in growth condition characteristics such as the leaf area, plant height, stem diameter, and leaf angle under water and fertilizer stress, because of the problems such as a data acquisition manner and field-of-view differences, leaf overlapping, target blockage in a plurality of targets, it is difficult to synchronously and effectively obtain morphological characteristics of the plant. The overall morphological characteristics of the plant can be synchronously obtained by using 3D laser scanning, and the precision may reach a micrometer level. Therefore, characteristic differences in the leaf area, plant height, stem diameter, and growth condition under nutrient stress can be extracted and analyzed.

In the present invention, apparent crop morphological characteristics on a canopy scale and polarized hyperspectral imaging characteristics on a canopy/leaf scale that are obtained through 3D laser scanning are integrated to monitor comprehensive growth condition of potted lettuce, so that the advantages of different scales and different monitoring methods can be combined, to achieve the innovativeness. Compared with the Prior Art, the Present Invention has the Following Beneficial Effects:

1. At present, water and fertilizer stress information is not considered in greenhouse environment regulation technology. In the present invention, a crop water and fertilizer stress monitoring technology that integrates polarized hyperspectral imaging and multi-scale information from 3D laser scanning is created, to overcome the limitation to current environmental control according to only environmental factor information. Because on-demand regulation can be performed, the fertilizer usage is greatly reduced, the environmental control cost and labor cost are reduced, and the economic benefit is improved.

2. In the present invention, polarized hyperspectral imaging and 3D laser scanning technologies are combined. Polarized hyperspectral images in different sensitive spectral bands on a lettuce leaf scale and differences in 3D scanning morphological characteristics such as the biomass, leaf area, plant height, stem diameter, and leaf angle on the crop canopy scale caused by different nitrogen stress levels are fully utilized. Internal and external characteristics on different scales are integrated and combined to perform inversion and quantitative analysis of water and fertilizer stress in lettuce, to improve the monitoring precision of water and fertilizer stress in lettuce and provide reference for the accurate management of facility water supply and fertilizer use based on growth information of crop.

1. sample; 2. dual-coordinate sample holder; 3. vertical boom: 3-1. base 1, 3-2. vertical rod, and 3-3. first slide; 4. cantilever: 4-1. base 2, 4-2. suspended rod, and 4-3. second slide; 5. polarized hyperspectral imaging system: 5-1. polarized hyperspectral imaging system 1, and 5-2. polarized hyperspectral imaging system 2; 6. tripod head; 7. visible light-near infrared light source; 8. movement controller; 9. image acquisition device; 10. light source controller; 11. control computer; 13. PC; 14. FireWire adapter; 15. FireWire cable; 16. handheld 3D scanning head; and 17. power supply module.

DETAILED DESCRIPTION OF THE EMBODIMENTS

The present invention is further described below with reference to the accompanying drawings and specific embodiments. However, the protection scope of the present invention is not limited thereto.

Figure 1:
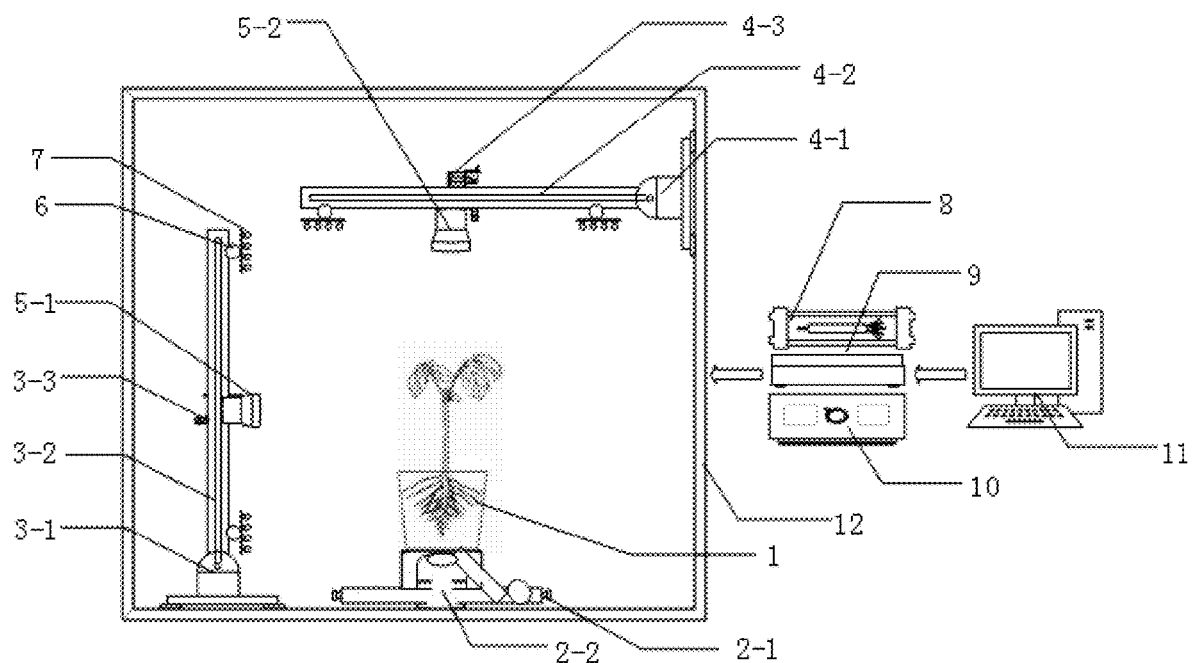
FIG. 1 is a schematic structural diagram of a polarized hyperspectral imaging system according to the present invention.
Figure 2:
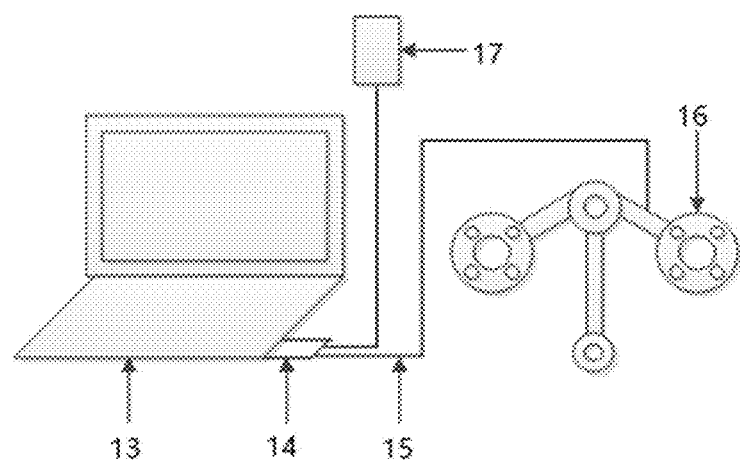
FIG. 2 is a schematic structural diagram of a 3D laser scanning system used in the present invention.

In the present invention, a polarized hyperspectral imaging system shown in FIG. 1 and a 3D laser scanning system shown in FIG. 2 acquire water and fertilizer information of potted lettuce on the leaf scale and canopy scale.

As shown in FIG. 1, a polarized hyperspectral imaging system includes a control system, a dual-coordinate sample holder 2, an image acquisition system, and a light source system.

The image acquisition system includes two polarized hyperspectral imaging systems 5, an image acquisition device 9, a vertical boom 3, and a cantilever 4. The vertical boom 3 consists of a base 3-1, a vertical rod 3-2 with a lead screw, and a first slide 3-3. The base 3-1 is fixed on the left side of the bottom of a light box 12 by a screw. The upper portion of the base 3-1 is connected to the vertical rod 3-2 by a hinge. The vertical rod 3-2 is swingable transversely with the hinge as the center, to complete the adjustment of the spatial pose of an imaging device. The first slide 3-3 is mounted on the vertical rod 3-2. A first polarized hyperspectral imaging system 5-1 is mounted on the first slide 3-3. The first slide 3-3 is movable vertically along the vertical rod 3-2 under the drive of the lead screw, to drive the first polarized hyperspectral imaging system 5-1 to search for an optimal monitoring position, to acquire polarized hyperspectral image information in the front-view direction.

The cantilever 4 consists of a base 4-1, a cross rod 4-2 with a lead screw, and a second slide 4-3. The base 4-1 is fixed at the upper portion of the right side plate of the light box 12 by a screw. The base 4-1 is connected to the cross rod 4-2 by a hinge. The cross rod 4-2 is swingable vertically with the hinge as the center, to complete the adjustment of the spatial pose of the imaging device. The second slide 4-3 is mounted on the cross rod 4-2. A second polarized hyperspectral imaging system 5-2 is mounted on the second slide 4-3. The second slide 4-3 is movable transversely in the horizontal direction along the cross rod 4-2 under the drive of the lead screw, to drive the second polarized hyperspectral imaging system 5-2 to search for an optimal monitoring position, to acquire the polarized hyperspectral image information in the top-view direction.

The light source system consists of a visible light-near infrared light source 7 and a tripod head 6. One tripod head 6 is respectively mounted at the bottom end and the top end of the vertical rod 3-2 and the right end and the left end of a vertical rod 4-2. The visible light-near infrared light source 7 is respectively mounted on each tripod head. The tilt of the visible light-near infrared light source 7 is capable of being set by using the tripod head 6, to implement clear and uniform imaging of the plant.

The dual-coordinate sample holder 2 is fixed at the geometric center position of the bottom plane of the light box 12. 2-1 is a horizontal lead screw. 2-2 is a vertical lead screw. A sample carrier is mounted at the top end of the vertical lead screw 2-2 and is used for placing a to-be-tested sample 1. The horizontal lead screw 2-1 and the vertical lead screw 2-2 move to drive the sample carrier to displace uniformly in the horizontal direction and the vertical direction, to cooperate with the image acquisition system to implement the scanning and imaging of the push broom polarized hyperspectral imaging system 5-1 and polarized hyperspectral imaging system 5-2.

The polarized hyperspectral imaging system 5 consists of a front polarizer, a polarizer driving apparatus, a front filter, a filter switching apparatus, a spectrograph, and an imaging system from front to rear. The polarizer is located at the foremost end of the entire system and is rotatable by 360° under the drive of the polarizer driving apparatus, to set any polarization angle. The spectrograph and the imaging system set the polarization angle and acquire polarization information. Narrowband filters of 402 nm, 446 nm, 556 nm, 636 nm, 699 nm, 706 nm, 775 nm, 960 nm, and 1420 nm are located behind the polarizer. A wheel switching manner is used for the filter, to cooperate with the spectrograph and the imaging system to acquire front-view and top-view hyperspectral feature images of a crop sample under nutrient and water stress.

The control system includes a control computer 11, a light source controller 10, the image acquisition device 9, and a movement controller 8.

The light source controller 10 is connected to the visible light-near infrared light source 7, to implement light source control with different light intensity and light quality. The image acquisition device 9 is connected to the two polarized hyperspectral imaging systems 5 and the control computer 11. The control computer 11 sends an instruction to acquire front-view and top-view imaging information of the polarized hyperspectral imaging system 5.

The movement controller 8 is connected to the dual-coordinate sample holder 2, the vertical boom 3, the cantilever 4, and the tripod head 6. At the same time, the movement controller 8 is connected to the control computer 11. The control computer 11 sends instructions to control the vertical displacement and the horizontal displacement of the dual-coordinate sample holder 2, control the slide drive of the vertical boom 3 and the cantilever 4, and control the tilt of the tripod head 6.

As shown in FIG. 2, the 3D scanning imaging system consists of a personal computer (PC) 13, a FireWire adapter 14, a FireWire cable 15, a handheld 3D scanning head 16, and a power supply module 17. The handheld 3D scanning head 16 is connected to the FireWire adapter 14 by the FireWire cable 15, and is connected to the PC by the FireWire adapter 14. PC software is used to implement 3D scanning control and information acquisition of the handheld 3D scanning head 16. The power supply module 17 is connected to the PC by the FireWire adapter 14 to supply power. The power supply module 17 is connected to the handheld 3D scanning head 16 to supply power to the handheld 3D scanning head 16.

The 3D laser scanning system is also connected to the control computer 11 and is used for acquiring 3D laser scanning and imaging data. A data processing module and a monitoring module are built in the control computer 11. The data processing module is configured to: repair a lettuce model according to the 3D laser scanning and imaging data, establish a biomass model, a leaf area model, a plant height model, and a stem diameter model of lettuce, and calculate the volume, leaf area, plant height, and stem diameter; and perform background segmentation on a polarized hyperspectral image and extract a feature wavelength according to polarized hyperspectral image data, to obtain the venation distribution, average grayscale, and leaf margin shaded area at nutrient- and water-sensitive wavelengths and polarization state, Stokes vector, Mueller matrix variables of feature images of 402 nm, 446 nm, 556 nm, 636 nm, 699 nm, 706 nm, 775 nm, 960 nm, and 1420 nm at characteristic polarization angles of 0°, 45°, 90°, 135°, and 180°. The monitoring module obtains comprehensive growth condition information of potted lettuce according to the data obtained by the data processing module, based on a lettuce water content prediction model and a nitrogen monitoring model, and according to a PLS nitrogen regression model that is based on original variables.

A method for monitoring comprehensive growth condition of potted lettuce in the present invention mainly includes the following steps:

Step 1: Culturing of Samples First

Water-stressed samples of lettuce are processed at four levels. 12 plants are used for each level. Concentrates with 25%, 50%, 75%, and 100% of the standard water content are respectively used for four water level irrigation amounts. There are four levels of nitrogen, which are respectively 25%, 50%, 100%, and 200% of that in the standard formula. 12 plants are used for each level. The samples are cultured in pots with perlite, and nutrients and water are supplied to samples by using a timed drip irrigation apparatus. During the seeding stage of crop, a nutrient solution is irrigated once in the morning every day. In the middle and later stages of the growth of crop, the nutrient solution is irrigated once in the morning and once in the afternoon every day, and irrigation lasts five minutes each time. The timed on or off of a timer is controlled to control the supply of the nutrient solution.

TABLE 1

Configuration table of a stock solution using a formula of a nutrient solution for lettuce

| Stock solution | Compound name | Compound usage (mg/L) | Concentration multiple | Compound usage in the stock solution (mg/L) |
|---|---|---|---|---|
| Solution A | $Ca(NO_3)_2 \cdot 4H_2O$ | 236 | 100 | 23.6 |
|  | $KNO_3$ | 404 |  | 40.4 |
| Solution B | $NH_4H_2PO_4$ | 57 | 100 | 5.7 |
|  | $MgSO_4 \cdot 7H$ | 123 |  | 12.3 |

TABLE 2

Configuration table of a stock solution using a formula of micronutrients

| Stock solution | Compound name | Compound usage (mg/L) | Concentration multiple | Compound usage in the stock solution (mg/L) |
|---|---|---|---|---|
| Solution C | EDTA-2NaFe | 20-40 | 1000 | 20-40 |
|  | $H_3BO_3$ | 2.86 |  | 2.86 |
|  | $MnSO_4 \cdot 4H_2O$ | 2.13 |  | 2.13 |
|  | $ZnSO_4 \cdot 7H_2O$ | 0.22 |  | 0.22 |
|  | $CuSO_4 \cdot 5H_2O$ | 0.08 |  | 0.08 |
|  | $(NH_4)6Mo_7O_{24} \cdot 4H_2O$ | 0.02 |  | 0.02 |

The formula of the standard nutrient solution for lettuce is shown in Table 1 and Table 2. Lettuce is processed at four nitrogen levels. Table 3 is a gradient compound usage table of nitrogen in lettuce: In a first group (A), based on the standard formula, without changing other nutrient elements, the amount of nitrogen element is reduced to 25% of that in the standard formula, and $Ca^{2+}$, $K^+$, and $PO_4^{-3}$ that are reduced along with the nitrogen element are supplemented by using $CaCl_2$), KCl, and $KH_2PO_4$. In a second group (B), based on the standard formula, the nitrogen element is reduced to 50% of that in the standard formula, and $Ca^{2+}$, $K^+$, and $PO_4^{-3}$ that are reduced along with the nitrogen element are supplemented by using $CaCl_2$, KCl, and $KH_2PO_4$. In a third group (C), a normal nutrient solution is configured according to the standard formula. In a fourth group (D), based on the standard formula, the nitrogen element is doubled, and the nitrogen element is supplemented by using $NaNO_3$ and $CO(NH_2)_2$.

TABLE 3

Gradient compound usage table of nitrogen in lettuce

| Gradient of N | $Ca(NO_3)_2 \cdot 4H_2O$ | $KNO_3$ | $NH_4H_2PO_4$ | $MgSO_4 \cdot 7H_2O$ | Add $CaCl_2$ | Add KCl | Add $KH_2PO_4$ | Add $NaNO_3$ | Add $CO(NH_2)_2$ |
|---|---|---|---|---|---|---|---|---|---|
| 25% | 59 | 101 | 14.38 | 123 | 83.25 | 195.56 | 51 |  |  |
| 50% | 118 | 202 | 28.75 | 123 | 55.5 | 130.38 | 34 |  |  |
| 100% | 236 | 404 | 57 | 123 |  |  |  |  |  |
| 200% | 236 | 404 | 57 | 123 |  |  |  | 510 | 15 |

Water-stressed samples are respectively processed in the following manner: In a first group (W1), a nutrient solution and water are supplied to crop by using a standard formula and a normal irrigation amount throughout the entire experiment. In a second group (W2), standard irrigation is performed twice during the experiment, the concentrate is only irrigated for one minute at 8 o'clock every day during the remaining time, and the concentrate is a nutrient solution that is obtained through proportional concentration according to a nutrient solution irrigation amount required for one day in a corresponding growth stage by using a standard nutrient solution formula and according to irrigation for one minute, to guarantee various nutrients required for the growth of the plant. In a third group (W3), standard irrigation is performed once in the middle stage of the experiment, and the concentrate is also only irrigated for one minute at 8 o'clock every day during the experiment. In a fourth group (W4), irrigation is not performed throughout the entire experiment, the concentrate is only applied for one minute every day. Processing manners of sample groups with different water content levels are shown in Table 4.

TABLE 4

Processing manners of sample groups with different water content levels in lettuce

| Water content | Nutrient solution | Drip irrigation time | Drip irrigation |
| --- | --- | --- | --- |
| W1 | Standard solution | Five minutes | Twice every day |
| W2 | Concentrate | 1 minute (sufficient) | Once every day |
| W3 | Concentrate | 1 minute (sufficient) | Once every day |
| W4 | Concentrate | 1 minute | Once every day |

Step 2: Acquisition of Morphological Data of an Entire Lettuce Plant 2.1 Acquisition of 3D Laser Scanning Imaging Data by Using a Handheld, Self-Positioning, 3D Laser Scanner 1) During scanning, black-contour high-reflectivity target dots with a diameter of 6 mm on a leaf and a pot of a crop to be scanned are first bonded, the shortest distance between two target dots being controlled to be 15 mm. There is a relatively flat surface on the pot. To reduce the time of bonding the target dots and improve the acquisition efficiency, the target dots are bonded to two semicircular pieces of white paper, the distance between the target dots is controlled to be 100 mm, and the two semicircular pieces of white paper are spliced into one circular piece and placed on the plane of the upper edge of a pot.

Figure 3:
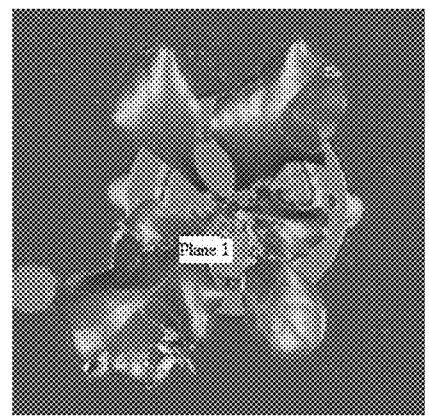
FIG. 3 is a diagram of repairing 3D scan data of lettuce.
Figure 3:
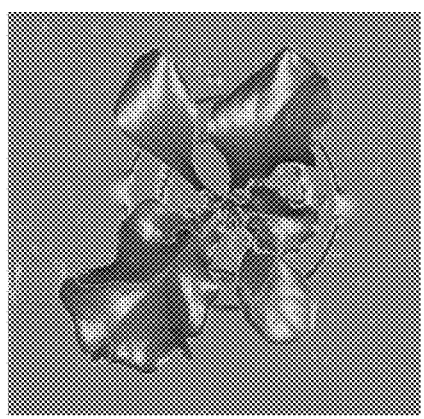
Figure 3:
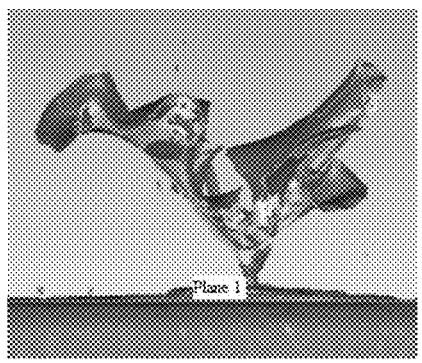
Figure 3:
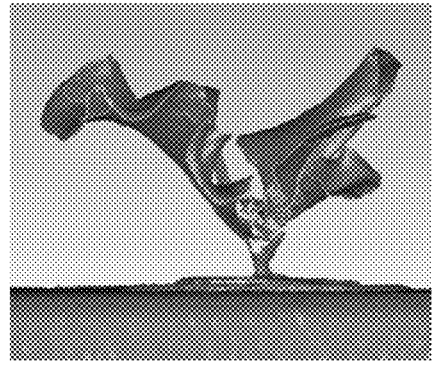

2) The scanner is operated, and a calibration board is measured by using the 3D laser scanner to correct parameters of a sensor, to ensure the precision of data acquisition. Before 3D laser scan data is acquired, the laser power and the shutter time of the sensor of the scanner and the resolution of the acquisition software need to be determined in advance to ensure a clear 3D model. After analysis and comparison, it is eventually set that the laser power is 65%, the shutter time is 7.2 ms, and the resolution is 0.50 mm. Eventually, 3D data of all crop samples is sequentially obtained in a handheld scanning mode. FIG. 3 shows the 3D morphology of lettuce plants acquired under set parameters and postprocessed images thereof.

2.2 Acquisition of Polarized Hyperspectral Imaging Data by Using a Polarized Hyperspectral Imaging System 1) A sample 1 is placed on a displacement stage 2 of the polarized hyperspectral imaging system, a wavelength range of a uniform light source system 7 is set to 300 nm to 2200 nm, a light intensity range is set to 6500 lux, and the geometric center of the imaging system is adjusted to be consistent with the geometric center of the horizontal axis X and the vertical axis Z of the displacement stage.

2) The two hyperspectral imaging systems 5-1 and 5-2 each having a front polarizing filter set are used, sampling polarization angles of polarizers being 0°, 45°, 90°, 135°, and 180°, transmission wavelengths of hyperspectral front filters being 402 nm, 446 nm, 556 nm, 636 nm, 699 nm, 706 nm, 775 nm, 960 nm, and 1420 nm, and push-broom, polarized hyperspectral scanning imaging is separately performed in the horizontal direction and the vertical direction, to obtain polarized hyperspectral feature images in the front-view direction and the top-view direction.

3) Hyperspectral feature images of a sample under nutrient and water stress in the front-view and top-view fields of view are extracted by performing coordinate matching and integration of front-view/top-view feature images, and images of the crown spread, plant height, and leaf angle of the plant are extracted.

4) Hyperspectral feature images of the canopy at characteristic wavelengths are extracted based on 402-nm, 446-nm, 556-nm, 636-nm, 699-nm, 706-nm, 775-nm, 960-nm, and 1420-nm front filters, and feature parameters such as the venation distribution, average grayscale, and leaf margin shaded area of the leaf surface at hyperspectral nutrient- and water-sensitive wavelengths of 402 nm, 446 nm, 556 nm, 636 nm, 699 nm, 706 nm, 775 nm, 960 nm, and 1420 nm are extracted.

5) Polarization state, Stokes vector, Mueller matrix variables of the plant sample under nitrogen and water stress are extracted based on obtained polarized hyperspectral images of 402 nm, 446 nm, 556 nm, 636 nm, 699 nm, 706 nm, 775 nm, 960 nm, and 1420 nm at characteristic polarization angles of 0°, 45°, 90°, 135°, and 180°.

Step 3: Processing and Analysis of Data 3.1 Modeling of the 3D Laser Scanning Imaging Data (1) A model is repaired by using the reverse engineering software Geomagic Qualify, to overcome scanning defects to obtain an optimal lettuce model.

1) The obtained 3D data of lettuce is imported into the software Geomagic Qualify, the lettuce model formed by triangles is converted into a point cloud, and excessive noise are eliminated by using the software.

2) The 3D point cloud is converted by encapsulation into a curved surface model formed by triangles, and hole parts in the surface of lettuce are filled.

3) Smoothing on the lettuce model is finally performed.

(2) The biomass, leaf area, plant height, and stem diameter of lettuce are modeled.

Volume Calculation

Figure 4:
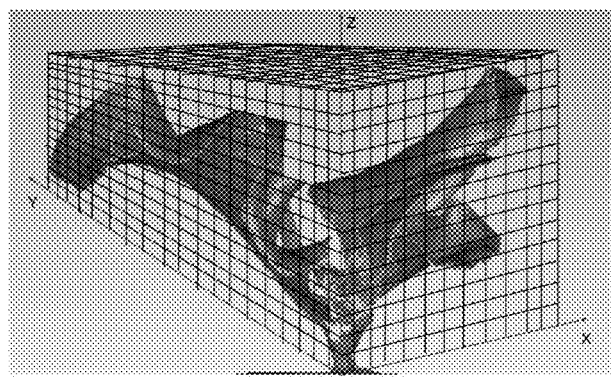
FIG. 4 shows a 3D space mesh model of lettuce.

As shown in FIG. 4, lettuce data is segmented at equal intervals with a step length of a in the plant height direction, that is, the Z axis direction, where the step length a is far less than the thickness of a lettuce leaf, to obtain n layers of lettuce segments. When a tends toward the infinitesimal, n tends toward infinity, and it may be considered that the volume of lettuce is formed by n layers of irregular graphs with the bottom area of $S_k$ and the height of a.

The cross-sectional area $S_k$ of each layer of segmented lettuce is calculated. Point cloud data of each layer of lettuce is projected onto an X-Y plane perpendicular to the plant height direction, and the data is segmented at equal intervals with a step length of a at the same time respectively in the X axis direction and the Y axis direction, to generate i×j pixel cells. Each pixel cell is determined according to point cloud data projected into the pixel cell of each layer of segmented lettuce, where when the pixel cell includes the projected point cloud data of the lettuce, the pixel cell is a valid pixel cell and is labeled as 1, or otherwise, when the pixel cell does not include the point cloud data, the pixel cell is labeled as 0. A quantity M of valid pixel cells is counted, and a product of multiplying the quantity of valid pixel cells by the area of a unit pixel cell is calculated as the cross-sectional area of the layer of lettuce. Formulas for calculating the volume of lettuce are:

$$S_k = aaM \tag{1}$$

and $$V = \sum_{i=1}^{n} S_k = \sum_{i=1}^{n} aaM \tag{2}$$

where
in the formulas, V is the volume of lettuce, $S_k$ is the cross-sectional area of lettuce, a is the step length, and M is the quantity of valid pixel cells.

A biomass monitoring model that is based on 3D scan data is established based on measured values of the obtained volume of the lettuce and the obtained fresh weight of the lettuce:

$$B_m = 0.13 + 0.91V \tag{3}$$

where
in the formula, $B_m$ is the biomass of the lettuce. A correlation coefficient of the model is 0.98, and a root-mean-square deviation is 0.26. The obtained volume of a lettuce plant and a biomass model are used in combination to implement the accurate inversion of biomass characteristics.

Leaf Area Calculation

The point cloud data is interpolated to form an irregular triangle mesh, the area $S_i$ of each triangle is calculated, and addition is performed on the areas to calculate the leaf area $S_c$. A formula for calculating the leaf area of lettuce is:

$$S_c = \sum_{i=1}^{n} S_i \tag{4}$$

Plant Height Calculation

It is assumed that the coordinates of any point in the point cloud data are f(x, y, z). It is only necessary to calculate the maximum value $z_{max}$ and the minimum value $z_{min}$ of the lettuce model in the Z axis direction. It is labeled that the coordinate point of the maximum value $z_{max}$ in this case is $f(x_1, y_1, z_1)$ and the coordinate point of the minimum value $z_{min}$ is $f(x_2, y_2, z_2)$. The distance between the two coordinate points is calculated by using the following formula to obtain the plant height $P_h$:

$$P_h = z_{max} - z_{min} = z_1 - z_2 \tag{5}$$

Stem Diameter Calculation

Lettuce stem cross sections are captured at intervals of 3.3 mm from the bottom of a permanent plant pot in the plant height direction, three cross sections are captured, the diameter of each cross section is calculated, and an average value of the cross sections is calculated to calculate the stem diameter of the lettuce.

Figure 5:
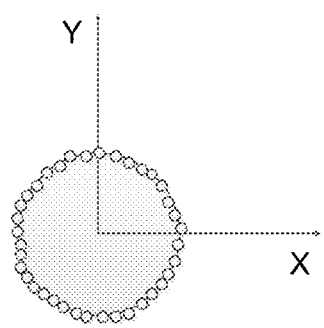
FIG. 5 shows the coordinates of the stem diameter of lettuce.

The image of the lettuce stem cross section is formed by a layer of point cloud approximate to a circle, and the maximum value $x_{max}$ and the minimum value $x_{min}$ in the X axis direction and the maximum value $y_{max}$ and the minimum value $y_{min}$ in the Y axis direction are calculated in the X-Y plane to calculate the diameter of the cross section. As shown in FIG. 5, a formula for calculating the stem diameter of the lettuce is:

$$L_a = \sum_{i=1}^{3} [(x_{i\,max} - x_{i\,min}) + (y_{i\,max} - y_{i\,min})]/6 \tag{6}$$

where
in the formula, $L_a$ is the stem diameter of the lettuce, $x_{imax}$ and $x_{imin}$ are respectively the maximum value and the minimum value of an $i^{th}$ layer (i=1, 2 or 3) of cross-sectional image in the X axis direction, and $y_{imax}$ and $y_{imin}$ are respectively the maximum value and the minimum value of the $i^{th}$ layer of cross-sectional image in the Y axis direction.

A lettuce nitrogen monitoring model is established by using a lettuce sample:

$$N = 13.26 - 0.24L_a + 0.15P_h + 7.1 \times 10^{-6} S_c + 0.03 B_m \tag{7}$$

where
a correlation coefficient of the model is 0.90, and a root-mean-square deviation is 0.87.

3.2 Modeling of Polarized Hyperspectral Image Data
(1) Background Segmentation is Performed on a Polarized Hyperspectral Image.

1) A characteristic that there is a largest grayscale difference between a target image at 476 nm and the background is used to segment a target image of lettuce by using a bimodal method.

2) Grayscale inversion is performed on a binarized target image, residues are filled, and solitary noise is eliminated.

3) A pixel multiplication operation is performed on the original hyperspectral image and the processed binarized target image, to eventually obtain a hyperspectral sequence target image of lettuce leaf.

(2) A Polarized Hyperspectral Feature Wavelength is Extracted.

1) Nitrogen features are screened by using a sensitive range stagewise and stepwise regression method, and indices are obtained from an image with variables of stepwise regression selection by using an ABS method.

2) An index list, that is, Table 5, is obtained according to the ABS method. Sorting is performed according to the values of the indices. Wavelengths with large image indices are eventually selected as nitrogen feature wavelengths, the wavelengths being 402 nm, 446 nm, 556 nm, 636 nm, 699 nm, and 706 nm.

3) Feature wavelengths that can best represent water are extracted by using the ABS method, and grayscale average values at the feature wavelengths of 775 nm, 960 nm, and 1420 nm are used for water features of the lettuce.

4) The venation distribution, average grayscale, and leaf margin shaded area at nutrient- and water-sensitive wavelengths and the polarization state, Stokes vector, Mueller matrix variables of feature images of 402 nm, 446 nm, 556 nm, 636 nm, 699 nm, 706 nm, 775 nm, 960 nm, and 1420 nm at characteristic polarization angles of 0°, 45°, 90°, 135°, and 180° are obtained.

TABLE 5

| Characteristic band and index in ABS | | |
|---|---|---|
| Wavelength | Index | Band number |
| 402 nm | 985.37 | 11 |
| 418 nm | 689.96 | 24 |

TABLE 5-continued

Characteristic band and index in ABS

| Wavelength | Index | Band number |
|---|---|---|
| 429 nm | 727.39 | 33 |
| 446 nm | 941.04 | 47 |
| 522 nm | 823.57 | 108 |
| 540 nm | 877.49 | 122 |

TABLE 5-continued

Characteristic band and index in ABS

| Wavelength | Index | Band number |
|---|---|---|
| 556 nm | 1088.58 | 135 |
| 569 nm | 723.89 | 145 |
| 615 nm | 575.31 | 182 |
| 636 nm | 906.55 | 198 |
| 650 nm | 873.21 | 209 |
| 685 nm | 796.35 | 236 |
| 699 nm | 991.87 | 247 |
| 706 nm | 998.22 | 253 |
| 741 nm | 370.43 | 280 |

Step 4: Correction of a Model by Using a Water Compensation Factor

The grayscale average values at the feature wavelengths of 775 nm, 960 nm, and 1420 nm are used to represent a water feature of lettuce. Water content features of crop nitrogen images in different characteristic spectral bands are analyzed. Water content response models of lettuce leaf in different characteristic spectral bands are established. A nitrogen feature of lettuce is compensated for. A specific process thereof is:

1) PLSR is performed on a grayscale variable of a water content feature image of a sample and a measured value of water content to establish a lettuce water content prediction model:

$$W = 65.09 + 43.82 AG_{775} + 12.65 AG_{960} - 117.72 AG_{1420} \quad (8),$$

where
in the formula, $AG_{775}$, $AG_{960}$, and $AG_{1420}$ represent grayscale average values of a lettuce leaf image at sensitive wavelengths of 775 nm, 960 nm, and 1420 nm, and W is a measured value of water content of leaf.

2) Hierarchical compensation of nitrogen features is performed according to a water content level of a prediction sample of the monitoring model and based on differences in reflection responses at different water content levels. In the case of an estimated water content level, a change rate $\Delta W_i$ of a nitrogen hyperspectral image eigenvariable $AG_i$ ($i=1, 2, \ldots,$ and 6) in the sample along with a water content level at the same nitrogen content level may be calculated by combining total nitrogen content in a sample obtained through AA3 chemical testing and a reflectivity value at a nitrogen optical spectrum feature wavelength, correction coefficients $\Delta AG_i$ for the eigenvariable $AG_i$ at different water content levels may be calculated accordingly, as shown in Table 6, and the nitrogen hyperspectral image eigenvariable $AG_i$ is corrected according to Formula (9).

TABLE 6

Water content change rate $\Delta W_i$ and correction coefficient $\Delta AG_i$ of hyperspectral image eigenvariables of nitrogen in lettuce

| Feature image | Change rate ($\Delta W_i$) | $\Delta AG_i$ W > 80% | 70% < W ≤ 80% | 60% < W ≤ 70% | W ≤ 60% |
|---|---|---|---|---|---|
| 402 nm | 2.08 × 10$^{-1}$ | 3.18 × 10$^{-3}$ | −4.95 × 10$^{-2}$ | −5.72 × 10$^{-2}$ | −8.06 × 10$^{-2}$ |
| 446 nm | 3.74 × 10$^{-1}$ | 1.85 × 10$^{-3}$ | −3.66 × 10$^{-2}$ | −4.05 × 10$^{-2}$ | −7.29 × 10$^{-2}$ |
| 556 nm | 8.52 × 10$^{-1}$ | 6.76 × 10$^{-2}$ | −7.13 × 10$^{-2}$ | −8.05 × 10$^{-2}$ | −5.97 × 10$^{-2}$ |
| 636 nm | 11.25 × 10$^{-1}$ | 8.28 × 10$^{-2}$ | −9.71 × 10$^{-2}$ | −4.38 × 10$^{-2}$ | −8.58 × 10$^{-2}$ |
| 699 nm | 9.76 × 10$^{-1}$ | 2.55 × 10$^{-2}$ | −9.64 × 10$^{-2}$ | −8.75 × 10$^{-2}$ | −8.07 × 10$^{-2}$ |
| 706 nm | 9.55 × 10$^{-1}$ | 2.69 × 10$^{-2}$ | −8.87 × 10$^{-2}$ | −8.49 × 10$^{-2}$ | −8.52 × 10$^{-2}$ |

$$AG_i' = AG_i^* (1 + \Delta AG_i), \ (i=1,2,\ldots, \text{and } 6) \quad (9).$$

3) The nitrogen monitoring model is established based on obtained hyperspectral image characteristics of lettuce nitrogen in different spectral bands, by using characteristic compensation, and by using a PLS method:

$$N = 23.39 + 6.14 AG_{402} + 25.66 AG_{446} - 31.52 AG_{556} + 66.85 AG_{636} + 45.65 AG_{699} - 56.76 AG_{706} \quad (10).$$

Step 5: Establishment of a Multi-Characteristic Integration Model

To fully utilize the complementary advantages of a plurality of characteristics and implement high-precision online monitoring of nitrogen in lettuce, information integration is performed based on the obtained polarized hyperspectral image characteristics and growth condition characteristics such as the stem diameter, plant height, leaf area, and biomass and by using PLSR, and a lettuce nitrogen multi-characteristic monitoring model is established.

1) To improve the balance and convergence speed of the model and eliminate model errors caused accordingly, normalization is first respectively performed on two different types of eigenvariables by using Formula (11):

$$x_i' = (x_i - x_{min})/(x_{max} - x_{min}) \quad (11),$$

where
in the formula, x is an eigenvalue of an eigenvector, i is an eigen number ($i=1, 2, 3, \ldots$), and $x_{min}$ and $x_{max}$ are respectively the minimum value and the maximum value of a sample eigenvalue in the eigenvector.

2) PLS correlation analysis is performed on normalized six image characteristics and four growth condition characteristics, and a PLS nitrogen regression model that is based on original variables is established:

$$N = -4.72 + 12.34 AG_{402} - 8.52 AG_{446} + 34.71 AG_{556} - 26.73 AG_{636} + 10.94 AG_{699} - 15.62 AG_{706} 7.53 L_a - 11.42 P_h - 15.91 S_c + 18.95 B_m \quad (12).$$

Figure 6:
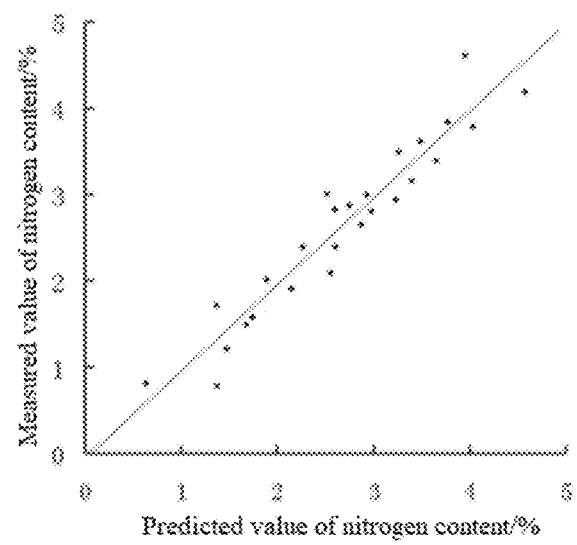
FIG. 6 shows a predicted value and a measured value of nitrogen content in lettuce.

As shown in FIG. 6, a correlation coefficient of a predicted value and a measured value of nitrogen in lettuce is 0.97, and a root-mean-square deviation is 0.39, to implement high-precision nutrient monitoring.

Step 6: Random sampling is performed to acquire information under water and fertilizer stress in actual greenhouse production work, Step 2 and Step 3 are repeated, data of crop under water and fertilizer stress is obtained, and the data is imported into the system for analysis and calculation, to obtain quantified results under nitrogen and water stress.

Step 7: Comprehensive growth condition information of potted lettuce is obtained by using quantified results under water and fertilizer stress and according to the PLS nitrogen regression model that is based on the original variables.

According to the method in the present invention, optimal regulation of water supply and fertilizer use in a greenhouse and environmental information is performed according to a crop model, a water and fertilizer regulation model, and an environmental regulation model.

The embodiments are the preferred implementations of the present invention. However, the present invention is not limited to the foregoing implementations. Any apparent improvement, replacement or variation made by a person skilled in the art without departing from the substantial content of the present invention falls within the protection scope of the present invention.

What is claimed is:

1. A method for monitoring a growth condition of a potted lettuce, comprising the following steps:
   step 1: culturing samples: cultivating the potted lettuce under a water stress, and cultivating the potted lettuce under a nitrogen stress and the water stress;
   step 2: acquiring morphological data of an entire lettuce plant according to the following steps:
   2.1 acquiring 3D laser scanning imaging data by using a handheld, a self-positioning, a 3D laser scanner according to the following steps:
      1) before scanning is performed, bonding black-contour high-reflectivity target dots with a diameter of 6 mm on a leaf and a pot of a crop to be scanned, a shortest distance between two of the black-contour high-reflectivity target dots being controlled to be 15 mm; and
      2) operating the 3D laser scanner, measuring a calibration board by using the 3D laser scanner to correct parameters of a sensor, and sequentially obtaining 3D data of all crop samples in a handheld scanning mode; and
   2.2 acquiring polarized hyperspectral imaging data by using a polarized hyperspectral imaging system according to the following steps:
      1) placing a sample on a displacement stage of the polarized hyperspectral imaging system, setting a wavelength range of a uniform light source system to 300 nm to 2200 nm, setting a light intensity range to 6500 lux, and adjusting a geometric center of the polarized hyperspectral imaging system to be consistent with a geometric center of a horizontal axis X and a vertical axis Z of the displacement stage;
      2) using two hyperspectral imaging systems and each of the two hyperspectral imaging systems having a front polarizing filter set, sampling polarization angles of polarizers being 0°, 45°, 90°, 135°, and 180°, transmission wavelengths of hyperspectral front filters being 402 nm, 446 nm, 556 nm, 636 nm, 699 nm, 706 nm, 775 nm, 960 nm, and 1420 nm, and separately performing a push-broom, a polarized hyperspectral scanning imaging in a horizontal direction and a vertical direction, to obtain polarized hyperspectral feature images in a front-view direction and a top-view direction;
      3) extracting the polarized hyperspectral feature images of the sample under a nutrient and water stress in front-view and top-view fields of a view by performing a coordinate matching and an integration of front-view/top-view feature images, and extracting images of a crown spread, a plant height, and a leaf angle of a plant;
      4) extracting the polarized hyperspectral feature images of a canopy at characteristic wavelengths based on 402-nm, 446-nm, 556-nm, 636-nm, 699-nm, 706-nm, 775-nm, 960-nm, and 1420-nm front filters, and extracting feature parameters such as a venation distribution, an average grayscale, and a leaf margin shaded area of a leaf surface at hyperspectral nutrient-sensitive wavelengths and hyperspectral water-sensitive wavelengths of 402 nm, 446 nm, 556 nm, 636 nm, 699 nm, 706 nm, 775 nm, 960 nm, and 1420 nm; and
   5) extracting a polarization state, a Stokes vector, Mueller matrix variables of the plant sample under the nitrogen stress and the water stress based on obtained polarized hyperspectral images of 402 nm, 446 nm, 556 nm, 636 nm, 699 nm, 706 nm, 775 nm, 960 nm, and 1420 nm at characteristic polarization angles of 0°, 45°, 90°, 135°, and 180°;
   step 3: processing and analyzing data according to the following steps:
   3.1 modeling the 3D laser scanning imaging data according to the following steps:
      (1) repairing a model by using a reverse engineering software, to overcome scanning defects to obtain an optimal lettuce model;
         1) importing obtained 3D data of the potted lettuce into the reverse engineering software, converting a lettuce model formed by triangles into a point cloud, and eliminating an excessive noise by using the reverse engineering software;
         2) converting the point cloud by an encapsulation into a curved surface model formed by the triangles, and filling hole parts in a surface of the potted lettuce; and
         3) finally performing smoothing on the lettuce model; and
      (2) modeling a biomass, a leaf area, a plant height, and a stem diameter of the potted lettuce:
      a volume calculation is as follows:
         1) segmenting lettuce data at equal intervals with a step length of a in a plant height direction, wherein the plant height direction is a Z axis direction, to obtain n layers of lettuce segments, wherein the step length a is less than a thickness of a lettuce leaf, when the step length a tends toward an infinitesimal, n tends toward infinity, and a volume of potted lettuce is formed by n layers of irregular graphs with a bottom area of $S_k$ and a height of a; and
         2) calculating a cross-sectional area $S_k$ of each layer of segmented lettuce: projecting point cloud data of the each layer of the segmented lettuce onto an X-Y plane perpendicular to the plant height direction, and segmenting the point cloud data at equal intervals with a step length of a at a same time respectively in the X axis direction and the Y axis direction, to generate i×j pixel cells; determining each pixel cell according to the point cloud data projected into the each pixel cell of the each layer of the segmented lettuce, wherein when the each pixel cell comprises a projected point cloud of the potted lettuce, the each pixel cell is a valid pixel cell and is labeled as 1, or, when the each pixel cell does not comprise the point cloud data, the each pixel cell is labeled as 0; and counting a quantity M of valid pixel cells, and calculating a product of multiplying the quantity of the valid pixel cells by an area of a unit pixel cell as the cross-sectional area of the each layer of the segmented lettuce, formulas for calculating the volume of potted lettuce being:

$$S_k = aaM \quad (1),$$

and $$V = \Sigma_{i=1}^{n} S_k = \Sigma_{i=1}^{n} aaM \quad (2),$$ wherein

V is the volume of potted lettuce, $S_k$ is the cross-sectional area of the segmented lettuce, a is the step length, and M is the valid pixel cells; and establishing, based on measured values of an obtained volume of the potted lettuce and an obtained fresh weight of the potted lettuce, a biomass monitoring model, wherein the biomass monitoring model is based on 3D scan data:

$$B_m = 0.13 + 0.91V \quad (3),$$ wherein $B_m$ is a biomass of the potted lettuce;

a leaf area calculation is as follows:
interpolating the point cloud data to form an irregular triangle mesh, calculating an area $S_i$ of each triangle, and performing addition on areas of the triangles to calculate the leaf area $S_c$, a formula for calculating the leaf area of the potted lettuce being:

$$S_c = \Sigma_{i=1}^{n} S_i \quad (4);$$

a plant height calculation is as follows:
assuming that coordinates of any point in the point cloud data are f(x, y, z), calculating a maximum value $z_{max}$ and a minimum value $z_{min}$ of the lettuce model in the Z axis direction, labeling a coordinate point of the maximum value $z_{max}$ is f(x1, y1, z1) and a coordinate point of the minimum value $z_{min}$ is f(x2, y2, z2), and calculating a distance between the two coordinate points by using the following formula to obtain the plant height $P_h$:

$$P_h = z_{max} - z_{min} = z_1 - z_2 \quad (5);$$

a stem diameter calculation is as follows:
capturing lettuce stem cross sections at intervals of 3.3 mm from a bottom of a permanent plant pot in the plant height direction, capturing three cross sections, calculating a diameter of each cross section, and calculating an average value of the three cross sections to calculate the stem diameter of the potted lettuce, wherein
an image of the lettuce stem cross section is formed by a layer of point cloud approximate to a circle, and a maximum value $X_{max}$ and a minimum value $x_{min}$ in the X axis direction and a maximum value $y_{max}$ and a minimum value $y_{min}$ in the Y axis direction are calculated in the X-Y plane to calculate a diameter of the lettuce stem cross section, a formula for calculating the stem diameter of the potted lettuce being:

$$L_a = \Sigma_{i=1}^{3}[(x_{i\,max} - x_{i\,min}) + (y_{i\,max} - y_{i\,min})]/6 \quad (6),$$ wherein $L_a$ is the stem diameter of the potted lettuce, $X_{max}$ and $X_{min}$ are respectively a maximum value and a minimum value of an $i^{th}$ layer (i=1, 2 or 3) of a cross-sectional image in the X axis direction, and $y_{max}$ and $y_{min}$ are respectively a maximum value and a minimum value of the $i^{th}$ layer of the cross-sectional image in the Y axis direction; and establishing a lettuce nitrogen monitoring model by using a lettuce sample:

$$N = 13.26 - 0.24L_a + 0.15P_h + 7.1 \times 10^{-6} S_c + 0.03 B_m \quad (7),$$ wherein a correlation coefficient of the lettuce nitrogen monitoring model is 0.90, and a root-mean-square deviation is 0.87; and 3.2 modeling polarized hyperspectral imaging data according to the following steps:
(1) performing a background segmentation on the polarized hyperspectral feature image according to the following steps;
1) using a characteristic, wherein the characteristic indicates a largest grayscale difference is between a target image at 476 nm and a background, to segment a target image of the potted lettuce by using a bimodal method;
2) performing a grayscale inversion on a binarized target image, filling residues, and eliminating a solitary noise; and
3) performing a pixel multiplication operation on an original hyperspectral image and a processed binarized target image, to obtain a hyperspectral sequence target image of the lettuce leaf; and
(2) extracting a polarized hyperspectral feature wavelength according to the following steps;
1) screening nitrogen features by using a sensitive range stagewise and stepwise regression method, and obtaining, by using an adaptive band selection (ABS) method, indices from an image with variables of a stepwise regression selection;
2) obtaining an index list according to the ABS method, performing a sorting according to values of the indices, and eventually selecting wavelengths with large image indices as nitrogen feature wavelengths, the nitrogen feature wavelengths being 402 nm, 446 nm, 556 nm, 636 nm, 699 nm, and 706 nm;
3) extracting, by using the ABS method, water feature wavelengths, and using grayscale average values at the water feature wavelengths of 775 nm, 960 nm, and 1420 nm for water features of the potted lettuce; and
4) obtaining the venation distribution, the average grayscale, and the leaf margin shaded area at the hyperspectral nutrient-sensitive wavelengths and the hyperspectral water-sensitive wavelengths and the polarization state, the Stokes vector, the Mueller matrix variables of the polarized hyperspectral feature images of 402 nm, 446 nm, 556 nm, 636 nm, 699 nm, 706 nm, 775 nm, 960 nm, and 1420 nm at the characteristic polarization angles of 0°, 45°, 90°, 135°, and 180°;

step 4: correcting a model by using a water compensation factor according to the following steps:
  using the grayscale average values at the polarized hyperspectral feature wavelengths of 775 nm, 960 nm, and 1420 nm to represent the water features of the potted lettuce, analyzing water content features of crop nitrogen images in different characteristic spectral bands, establishing water content response models of the lettuce leaf in the different characteristic spectral bands, and compensating for the nitrogen features of the potted lettuce, a specific process of compensating for the nitrogen features of the potted lettuce being:
  1) performing a partial least squares regression (PLSR) on a grayscale variable of a water content feature image of the sample and a measured value of the water content to establish a lettuce water content prediction model:

$$W=65.09+43.82AG_{775}+12.65AG_{960}-117.72AG_{1420} \quad (8),$$ wherein $AG_{775}$, $AG_{960}$, and $AG_{1420}$ represent the grayscale average values of a lettuce leaf image at sensitive wavelengths of 775 nm, 960 nm, and 1420 nm, respectively, and W is a measured value of a water content of the lettuce leaf;

2) performing a hierarchical compensation of the nitrogen features according to a water content level of a prediction sample of the lettuce nitrogen monitoring model and based on differences in reflection responses at different water content levels, wherein in a case of an estimated water content level, a change rate $\Delta W_i$ of a nitrogen hyperspectral image eigenvariable $AG_i$ (i=1, 2, . . . , and 6) in the sample along with a water content level at a same nitrogen content level are calculated by combining a total nitrogen content in a sample obtained through AA3 chemical testing and a reflectivity value at a nitrogen optical spectrum feature wavelength, correction coefficients $\Delta AG_i$ for the nitrogen hyperspectral eigenvariable $AG_i$ at the different water content levels are calculated accordingly, and the nitrogen hyperspectral image eigenvariable $AG_i$ is corrected according to formula (9):

$$AG_i'=AG_i*(1+\Delta AG_i), (i=1,2, \ldots, \text{ and } 6) \quad (9); \text{ and}$$

3) establishing the lettuce nitrogen monitoring model based on obtained hyperspectral image characteristics of a lettuce nitrogen in different spectral bands, by using characteristic compensation, and by using a partial least squares (PLS) method:

$$N=23.39+6.14AG_{402}+25.66AG_{446}-31.52AG_{556}+66.85AG_{636}+45.65AG_{699}-56.76AG_{706} \quad (10);$$

step 5: establishing a multi-characteristic integration model according to the following steps:
  performing an information integration based on an obtained polarized hyperspectral image characteristics and growth condition characteristics such as the stem diameter, the plant height, the leaf area, and the biomass and by using the PLSR, and establishing a lettuce nitrogen multi-characteristic monitoring model according to the following steps;

1) first respectively performing normalization on two different types of eigenvariables by using formula (11):

$$x_i'=(x_i-x_{min}(x_{max}-x_{min}) \quad (11), \text{ wherein}$$

x is an eigenvalue of an eigenvector, i is an eigen number (i=1, 2, 3, . . . ), and $x_{min}$ and $x_{max}$ are respectively a minimum value and a maximum value of a sample eigenvalue in the eigenvector; and 2) performing a PLS correlation analysis on normalized six image characteristics and four growth condition characteristics, and establishing a PLS nitrogen regression model that is based on original variables:

$$N=-4.72+12.34AG_{402}-8.52AG_{446}+34.71AG_{556}-26.73AG_{636}+10.94AG_{699}-15.62AG_{706}+7.53L_a-11.42P_h-15.91S_c+18.95B_m \quad (12);$$

step 6: performing a random sampling to acquire information under the water stress and a fertilizer stress in an actual greenhouse production work, repeating step 2 and step 3, obtaining data of a crop under the water stress and the fertilizer stress, and importing the data into a data processing module for an analysis and a calculation, to obtain quantified results under the nitrogen stress and the water stress; and step 7: obtaining growth condition information of the potted lettuce by using quantified results under the water stress and the fertilizer stress and according to the PLS nitrogen regression model, wherein the PLS nitrogen regression model is based on the original variables.

2. The method according to claim 1, wherein the potted lettuce is cultivated under the water stress at four levels in step 1, concentrates with 25%, 50%, 75%, and 100% of a standard water content are respectively used for four water level irrigation amounts, water-stressed samples are respectively processed in the following manner: in a first group, a nutrient solution and water are supplied to the crop by using a standard formula and a normal irrigation amount throughout an entire experiment; in a second group, a standard irrigation is performed twice during the entire experiment, a concentrate is irrigated for one minute at 8 o'clock every day during a remaining time, and the concentrate is the nutrient solution, wherein the nutrient solution is obtained through a proportional concentration according to a nutrient solution irrigation amount required for one day in a corresponding growth stage by using a standard nutrient solution formula and according to an irrigation for one minute, to guarantee various nutrients required for a growth of the plant; in a third group, the standard irrigation is performed once in a middle stage of the entire experiment, and the concentrate is only irrigated for one minute at 8 o'clock every day during the entire experiment; and in a fourth group, the irrigation is not performed throughout the entire experiment, the concentrate is applied for one minute every day.

3. The method according to claim 1, wherein the potted lettuce is cultivated under the nitrogen stress at four levels in step 1, a nitrogen content at the four levels is respectively 25%, 50%, 100%, and 200% of that in a standard formula, and nutrients and water are supplied to samples by using a timed drip irrigation apparatus; during a seeding stage of the crop, a nutrient solution is irrigated once in the morning every day; in a middle stage and a later stage of a growth of the crop, the nutrient solution is irrigated once in the morning and once in the afternoon every day, and an irrigation lasts five minutes each time; a timed on or off of a timer is controlled to control a supply of the nutrient solution; and the four levels are specifically: in a first group, based on the standard formula, without changing other nutrient elements, an amount of a nitrogen element is reduced to 25% of the nitrogen content in the standard formula, and $Ca^{2+}$, $K^+$, and $PO_4^{-3}$ are reduced along with the nitrogen element and are supplemented by using $CaCl_2$, $KCl$, and $KH_2PO_4$; in a second group, based on the standard formula, the nitrogen element is reduced to 50% of the nitrogen content in the standard formula, and $Ca^{2+}$, $K^+$, and $PO_4^{-3}$ are reduced along with the nitrogen element and are supplemented by using $CaCl_2$, $KCl$, and $KH_2PO_4$; in a third group, a normal nutrient solution is configured according to the standard formula; and in a fourth group, based on the standard formula, the nitrogen element is doubled, and the nitrogen element is supplemented by using $NaNO_3$ and $CO(NH_2)_2$.

4. The method according to claim 1, wherein during an acquisition of the 3D laser scanning imaging data in step 2, the black-contour high-reflectivity target dots are bonded to two semicircular pieces of a white paper, a distance between the black-contour high-reflectivity target dots is controlled to be 100 mm, and the two semicircular pieces of the white paper are spliced into one circular piece and placed on a plane of an upper edge of a pot.

5. The method according to claim 1, wherein during an acquisition of the 3D laser scanning imaging data, a laser power of the 3D laser scanner is 65%, a shutter time is 7.2 ms, and a resolution is 0.50 mm.

6. An apparatus for monitoring growth condition of potted lettuce according to claim 1, comprising a polarized hyperspectral image monitoring system, a 3D laser scanning system, a data processing module, and a monitoring module, wherein the polarized hyperspectral image monitoring system comprises a control system, a dual-coordinate sample holder, an image acquisition system, and a light source system;

the image acquisition system comprises two polarized hyperspectral imaging systems, an image acquisition device, a vertical boom, and a cantilever; wherein the vertical boom consists of a first base, a vertical rod with a first lead screw, and a first slide, wherein the first base is fixed on a left side of a bottom of a light box by a first screw, an upper portion of the first base is connected to the vertical rod by a hinge, and the vertical rod is swingable transversely with the hinge as a center, to complete an adjustment of a spatial pose of an imaging device; the first slide is mounted on the vertical rod; and a first polarized hyperspectral imaging system is mounted on the first slide, and the first slide is movable vertically along the vertical rod under a drive of the first lead screw, to drive the first polarized hyperspectral imaging system to search for an optimal monitoring position, to acquire polarized hyperspectral image information in the front-view direction;

the cantilever consists of a second base, a cross rod with a second lead screw, and a second slide, the second base is fixed at an upper portion of a right side plate of the light box by a second screw, the second base is connected to the cross rod by the hinge, and the cross rod is swingable vertically with the hinge as the center, to complete the adjustment of the spatial pose of the imaging device; and the second slide is mounted on the cross rod, a second polarized hyperspectral imaging system is mounted on the second slide, and the second slide is movable transversely in a horizontal direction along the cross rod under a drive of the second lead screw, to drive the second polarized hyperspectral imaging system to search for the optimal monitoring position, to acquire the polarized hyperspectral image information in the top-view direction;

the light source system consists of a visible light-near infrared light source and a tripod head, the tripod head is mounted at each of a bottom end and a top end of the vertical rod and a right end and a left end of a cross rod, the visible light-near infrared light source is mounted on the tripod head, and a tilt of the visible light-near infrared light source is set by using the tripod head, to implement clear and uniform imaging of the plant;

the dual-coordinate sample holder is fixed at a geometric center position of a bottom plane of the light box, wherein the dual-coordinate sample holder comprises a horizontal lead screw, a vertical lead screw, a sample carrier is mounted at a top end of the vertical lead screw and is used for placing a to-be-tested sample, and the horizontal lead screw and the vertical lead screw move to drive the sample carrier to displace uniformly in the horizontal direction and the vertical direction, to cooperate with the image acquisition system to implement a scanning and an imaging of a first push broom polarized hyperspectral imaging system and a second push broom polarized hyperspectral imaging system;

the polarized hyperspectral imaging system consists of a front polarizer, a polarizer driving apparatus, a front filter, a filter switching apparatus, a spectrograph, and an imaging system from a front to a rear, the front polarizer is located at a foremost end of the polarized hyperspectral imaging system and is rotatable by 360° under a drive of the polarizer driving apparatus, to set a polarization angle, and the spectrograph and the imaging system set the polarization angle and acquire polarization information; and narrowband filters of 402 nm, 446 nm, 556 nm, 636 nm, 699 nm, 706 nm, 775 nm, 960 nm, and 1420 nm are located behind the front polarizer, and a wheel switching manner is used for the front filter, to cooperate with the spectrograph and the imaging system to acquire front-view and top-view hyperspectral feature images of the crop sample under the nutrient stress and the water stress;

the control system comprises a control computer, a light source controller, the image acquisition device, and a movement controller;

the light source controller is connected to the visible light-near infrared light source, to implement a light source control with different light intensities and different light quality;

the image acquisition device is connected to the two polarized hyperspectral imaging systems and the control computer, and the control computer sends an instruction to acquire front-view and top-view imaging information of the polarized hyperspectral imaging system;

the movement controller is connected to the dual-coordinate sample holder, the vertical boom, the cantilever, and the tripod head; and at a same time, the movement controller is connected to the control computer, and the control computer sends instructions to control a vertical displacement and a horizontal displacement of the dual-coordinate sample holder, control a slide drive of the vertical boom and the cantilever, and control a tilt of the tripod head;

the 3D laser scanning system is connected to the control computer and is used for acquiring the 3D laser scanning and imaging data; and the data processing module and the monitoring module are built in the control computer, the data processing module is configured to: repair the lettuce model according to the 3D laser scanning and imaging data, establish a biomass model, a leaf area model, a plant height model, and a stem diameter model of the potted lettuce, and calculate the volume, the leaf area, the plant height, and the stem diameter; and perform the background segmentation on the polarized hyperspectral image and extract a feature wavelength according to the polarized hyperspectral imaging data, to obtain the venation distribution, the average grayscale, and the leaf margin shaded area at the nutrient-sensitive wavelengths and the water-sensitive wavelengths and the polarization state, the Stokes vector, the Mueller matrix variables of the polarized hyperspectral feature images of 402 nm, 446 nm, 556 nm, 636 nm, 699 nm, 706 nm, 775 nm, 960 nm, and 1420 nm at the characteristic polarization angles of 0°, 45°, 90°, 135°, and 180°; and the monitoring module obtains growth condition information of the potted lettuce according to the data obtained by the data processing module, based on the lettuce water content prediction model and the lettuce nitrogen monitoring model, and according to the PLS nitrogen regression model, wherein the PLS nitrogen regression model is based on the original variables, wherein the lettuce water content prediction model is:

$$W=65.09+43.82AG_{775}+12.65AG_{960}-117.72AG_{1420},$$

the lettuce nitrogen monitoring model is:

$$N=23.39+6.14AG_{402}+25.66AG_{446}-31.52AG_{556}+66.85AG_{636}+45.65AG_{699}-56.76AG_{706}, \text{ and}$$

the PLS nitrogen regression model based on the original variables is:

$$N=-4.72+12.34AG_{402}-8.52AG_{446}+34.71AG_{556}-26.73AG_{636}+10.94AG_{699}-15.62AG_{706}+7.53L_a-11.42P_h-15.91S_c+18.95B_m.$$

* * * * *